(12) United States Patent
Wiese et al.

(10) Patent No.: US 6,603,047 B2
(45) Date of Patent: Aug. 5, 2003

(54) CONDENSATION OF ALDEHYDES WITH KETONES BY MULTIPHASE REACTION

(75) Inventors: Klaus-Diether Wiese, Haltern (DE); Wilfried Buschken, Haltern (DE); Guido Protzmann, Zwingenberg (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/068,955

(22) Filed: Feb. 11, 2002

(65) Prior Publication Data
US 2002/0161264 A1 Oct. 31, 2002

(30) Foreign Application Priority Data

Feb. 10, 2001 (DE) .......................................... 101 06 186

(51) Int. Cl.⁷ .......................... C07C 45/73; C07C 29/14
(52) U.S. Cl. ........................ 568/345; 568/350; 568/390; 568/396; 568/880
(58) Field of Search ................................. 568/345, 350, 568/390, 396, 880

(56) References Cited

U.S. PATENT DOCUMENTS

| 5,583,263 A | 12/1996 | Muthusamy et al. | ....... 568/396 |
|---|---|---|---|
| 6,340,778 B1 | 1/2002 | Bueschken et al. | ......... 568/463 |

FOREIGN PATENT DOCUMENTS

| DE | 2 150 992 | 4/1973 |
|---|---|---|
| EP | 0 792 862 A1 | 9/1997 |
| EP | 0 816 321 A1 | 1/1998 |
| EP | 1 057 524 | 12/2000 |
| EP | 1 057 525 | 12/2000 |
| EP | 1 106 596 | 6/2001 |
| WO | WO 91/07368 | 5/1991 |

OTHER PUBLICATIONS

W. Kast, Darmstadt, VDI Wärmeatlas, "Allgemeine Gleichung des Druckverlusts",Aug. 8, 1997, pp. La1–Le4.

Noel Midous et al., "Flow pattern, Pressure Loss and Liquid Holdup Data in Gas–Liquid Downflow Packed Beds With Foaming And Nonfoaming Hydrocarbons", Journal Of Chemical Engineering Of Japan, vol. 9, No. 5, 1976, pp. 350–356.

R. P. Larkins et al., "Two–Phase Concurrent Flow in Packed Beds", A.I.Ch.E. Journal, vol. 7, No. 2, Jun. 1961, pp. 231–239.

Yuji Sato et al., "Pressure Loss And Liquid Holdup In Packed Bed Reactor With Cocurrent Gas–Liquid Down Flow", Journal Of Chemical Engineering Of Japan, vol. 6, No. 2, 1973. pp. 147–152.

D. E. Sweeney, "A Correlation for Pressure Drop in Two–Phase Cocurrent Flow in Packed Beds", AIChE Journal, vol. 13, No. 4, Jul. 1967, pp. 663–669.

Sabri Ergun, "Fluid Flow Through Packed Columns", Chemical Engineering Progress, vol. 48, No. 2, Feb. 1952, pp. 89–94.

Vern W. Weekman, Jr. et al., "Fluid–Flow Characteristics of Concurrent Gas–Liquid Flow in Packed Beds", A.I.Ch.E. Journal, vol. 10, No. 6, Nov. 1964, pp. 951–957.

Heinz Brauer, Grundlagen der Einhpasen– und Mehrphasenströmungen, Verlag Sauerländer, Aarau and Frankfurt/Main, 1971.

*Primary Examiner*—Samuel Barts
*Assistant Examiner*—Sikarl A. Witherspoon
(74) *Attorney, Agent, or Firm*—Oblon, Spivak, McClelland, Maier & Neustadt, P.C.

(57) ABSTRACT

A process for conducting multiphase reactions, especially the preparation of α,β-unsaturated ketones by condensation of aldehydes with ketones.

25 Claims, 1 Drawing Sheet

US 6,603,047 B2

CONDENSATION OF ALDEHYDES WITH KETONES BY MULTIPHASE REACTION

BACKGROUND OF THE INVENTION

1. Field of the Invention

The present invention relates to a process for conducting multiphase reactions, especially the preparation of α,β-unsaturated ketones by condensation of aldehydes with ketones.

2. Discussion of the Background

α,β-Unsaturated ketones are very reactive and hence used in a multiplicity of organic syntheses. For example, they are intermediates for the preparation of scents and pharmaceuticals.

It is known from Houben-Weyl, Methoden der organischen Chemie, Volume 7/1, pages 77 ff, and Organic Reactions, Volume 16, pages 27–47, 69–78, 177 ff, that aldehydes can be reacted with ketones to form α,β-unsaturated ketones. Temperatures of 5 to 25° C. are preferred for these condensations (Organic Reactions, loc. cit., page 77). The numerous catalysts employed in these processes, for example alkali and alkaline earth metal hydroxides, organic bases, alkali metal salts, alkoxides, also catalyze the self-condensation of the aldehydes or ketones and therefore lead to by-products as well. The workup of such mixtures is costly and inconvenient, since the catalyst used has to be removed again or neutralized. Target product yields are frequently unsatisfactory.

DE 2150992 describes a process for preparing α,β-unsaturated ketones from formaldehydes and ketones. The aldol condensation is catalyzed by a catalyst consisting essentially of zinc oxide. The reaction is carried out at temperatures of 140° C. to 200° C. The ketone is used in excess. The reaction mixture is worked up by distillation. Molar ratios in the range from 1.3/1 to 5.7/1 between the ketone and aldehyde provide conversions of 66% to 82%, based on the aldehyde used in deficiency, while α,β-unsaturated ketones are obtained in selectivities of 75% to 93%, depending on the identity of the materials used. Since the reaction mixtures contain only 20% to 60% of the target product, the separation cost and inconvenience is considerable.

EP 0792 862 A1 discloses a process for reacting aldehydes with ketones over a complex magnesium aluminum hydroxide. The aldehyde, which is used in deficiency, combines with the ketone used to form not only the aldol addition but also the aldol condensation product in a molar ratio in the range from 0.7/1 to 1.40/1. These two products are formed together in a selectivity, based on aldehyde, of only 71% to 79% at an aldehyde conversion of 96% to 98%.

U.S. Pat. No. 5,583,263 describes a two stage process for producing α,β-unsaturated ketones, especially the reaction of n-butyraldehyde with acetone. The first stage comprises reacting the reactant mixture, which contains acetone in excess, over a basic ion exchange resin to form β hydroxy ketones. n-Butyraldehyde is converted into 4-hydroxyheptanone in a selectivity of up to 88% at complete conversion. At the same time, diacetone alcohol is by-produced from acetone in a selectivity of up 95%. The crude mixture of the first stage is dehydrated in the second stage under acid catalysis to form the α,β-unsaturated ketones. The catalysts used are strong acids or a strongly acidic ion exchange resin. The yield of hept-3-en-2-one, the condensation product of n-butyraldehyde and acetone, is 85%, based on n-butyraldehyde. The diacetone is converted into mesityl oxide. This process is accordingly a process for coproducing two α,β-unsaturated ketones. The use of this process is disadvantageous when only one aldol condensation product, especially that of aldehyde and ketone, is the target product.

WO 91/07368 discloses a further two stage process for preparing α,β-unsaturated ketones from aldehydes and acetone. The first stage comprises reacting the aldehyde with acetone, used in excess, under catalysis by cyclic amines (perhydroisoindole and pyrrolidine derivatives) in the presence of water to form the corresponding β-hydroxyketone. After aldol addition has taken place, aqueous mineral acid (sulfuric acid, hydrochloric acid) is used to set a pH of 4.5 and a mixture of acetone and water is distilled off. The crude mixture is converted to the target product by elimination of water by admixing the crude mixture with a mixture of hydrochloric acid and chloroform and refluxing it. The target product is isolated by phase separation, washing and distillation. The yields of α,β-unsaturated methyl ketones, based on aldehyde used, are between 80% and 90%. Disadvantages of this process are especially the high workup cost and inconvenience and the use and consumption of auxiliary materials.

EP 0 816 321 A1 discloses preparing α,β-unsaturated methyl ketones by crossed aldol condensation of aldehydes with acetone in a batch operation. The catalyst used is 2% aqueous sodium hydroxide solution, and acetone is used in excess. The reaction takes place in the temperature range 70–72° C., and the reaction time is about 4.5 h. When isovaleraldehyde is reacted with acetone, for example, 6-methyl-3-hept-2-one and 6-methyl-4-hydroxyheptan-2-one are obtained in 66% and 3.3% yield respectively, based on isovaleraldehyde, the conversion of which is 98.3%. The process has the disadvantages that it is a batch process and that the yield of target product is unsatisfactory.

The abovementioned processes are unconvincing with regard to cost convenience and/or space-time yields.

OBJECT OF THE INVENTION

It is an object of the present invention to develop a more economical process.

SUMMARY OF THE INVENTION

The processes mentioned above involve at least one multiphase reaction (solid-liquid or liquid-liquid). The inventors have improved the multiphase reaction, especially that between substantially immiscible liquids.

DETAILED DESCRIPTION OF THE INVENTION

Figure 1:
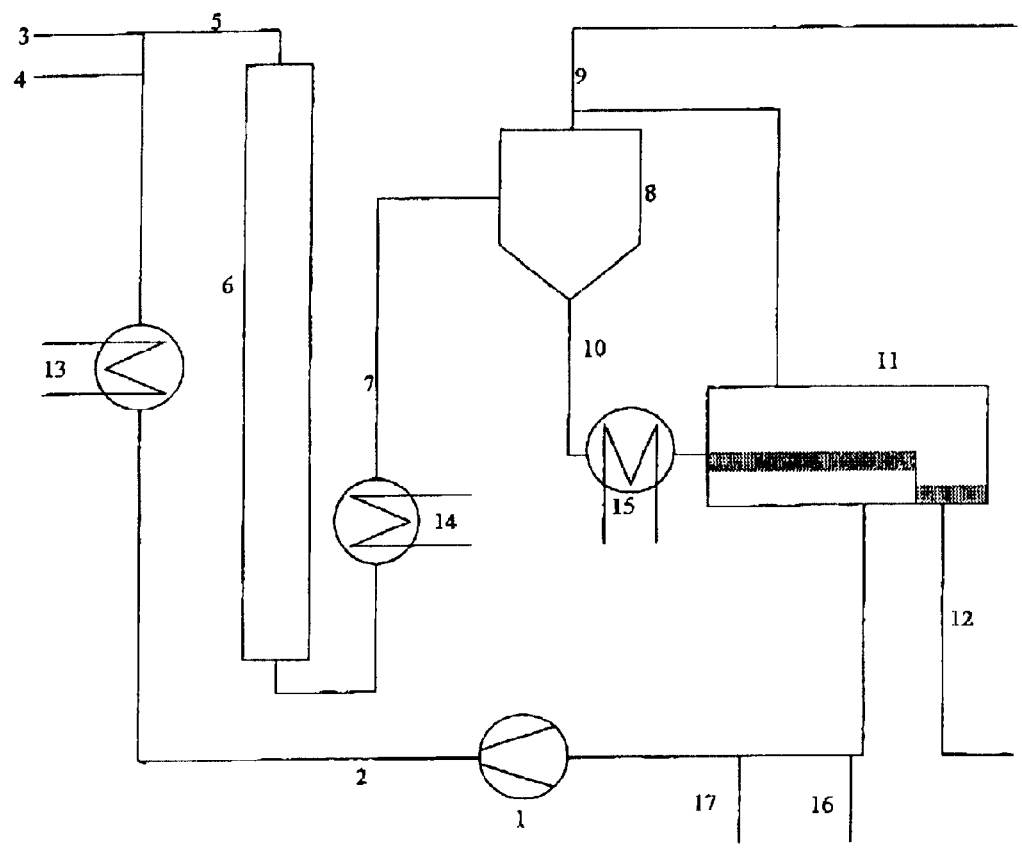
FIG. 1 describes an apparatus in which the invention process may be carried out.

In what follows, a two phase reaction is a reaction involving two immiscible or partly miscible fluidic phases. The aldol condensation of an aldehyde and a ketone involves two liquid phases which are immiscible or have a miscibility gap, and thus constitutes a two phase reaction. The two phases consist of reactant and catalyst solution at the start of the reaction and of product and catalyst phase after the reaction has taken place. During the reaction the catalyst phase is a continuous phase, in which the educt and product containing organic phase is dispersed.

Every two phase reaction presents a mass transfer problem. The reactants have to be transported into and the products out of the catalyst phase. Since transport processes are frequently slower than the actual reaction, such reactions are determined by the rate of mass transfer and so are referred to as mass transfer limited reactions.

For a two phase reaction, especially a two phase reaction where the phases are substantially insoluble in each other, to provide industrially acceptable space-time yields, the materials have to be brought into very intimate contact with each other. A very large mass transfer area $a_s$ has to be created between the phases. On the other hand, the phases have to be easily separable again after the reaction has taken place. Excessive mixing can lead to difficulties here, since emulsions can be formed. Most catalysts are solid and must be solved in an appropriate solvent.

As well as a large mass transfer area $a_s$, a very high mass transfer coefficient $k_l$ should be achieved in all multiphase reactions. Overall, the KLA value, i.e., the product of $k_l$ and $a_s$, in the mass transfer equation $$j = k_l * a_s * (C^* - C)$$

where
- $j$ [mol/s] is the molar stream of the reacting component passing through the phase interface,
- $k_l$ [m/s] is the mass transfer coefficient,
- $a_s$ [m²] is the phase interface area in the reactor,
- $C^*$ [mol/m³] is the maximum solubility of the reactant in the second phase and
- $C$ [mol/m³] is the actual concentration of the reactant and is in turn coupled with the reaction rate, should be maximal.

A further problem with multiphase reactions is the removal of heat in the case of exothermic reactions. Once the reaction rate has been successfully raised by improving the mass transfer, more heat will naturally have to be removed as well, which can lead to an undesirable temperature increase and even cause a reaction to run away.

For this reason, the two phase aldol condensation is frequently carried out in a stirred tank. With a stirred tank, there is no alternative but to accept the continual backmixing which reduces the effective concentration of the reactants and hence the space-time yield. This disadvantage has to be paid for with costly reaction space.

A two phase reaction could also be carried out in a flow tube, in which case there is a danger that the phases will separate and so substantially depress the reaction rate.

The invention process avoids the aforementioned disadvantages and is simple in engineering terms.

In engineering terms, the invention process meets the following preferred requirements of a multiphase process:
- Produce a high and stable mass transfer between the phases involved
- Be simple to implement, ideally using customary industrial equipment
- Simple and safe heat removal
- High consistency of operation
- Simple and safe scaleup With regard to the intended preparation of α,β-unsaturated ketones, there are additionally specific requirements:
- High selectivity, avoidance of high boiling α,β-products in particular
- Minimal formation of aldehyde—aldehyde secondary products
- Minimal formation of ketone—ketone secondary products
- High space-time yield, small reactors The process according to the invention is a surprisingly simple process for conducting two phase reactions which is performable in a tubular reactor—optionally containing packing elements or internal fitments—and is useful for the aldol condensation of an aldehyde with a ketone to form unsaturated ketones in high space-time yields and selectivities.

The present invention accordingly provides a process for preparing α,β-unsaturated ketones of the general structure I

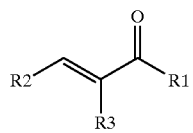

where R1 and R2 each independently represent a branched or unbranched, saturated or unsaturated aliphatic or cycloaliphatic-aliphatic hydrocarbon radical of 1 to 20, preferably 1 to 16, carbon atoms or a saturated or unsaturated cycloaliphatic hydrocarbon radical of 5 to 12 carbon atoms which may contain alkyl groups as substituents and/or an endoalkylene group or else each represent an araliphatic hydrocarbon radical of 7 to 15 carbon atoms, preferably a benzyl group, or an aromatic hydrocarbon radical, preferably a phenyl group, R3 represents hydrogen or an aliphatic hydrocarbon radical of 1 to 10 carbon atoms, or else R1 and R3 can combine with the two adjacent carbon atoms to form members of a common alicyclic ring and, furthermore, in R1, R2 and R3, one or more methylene groups which are not u-disposed relative to a carbonyl group may be substituted by an oxygen or sulfur atom, which comprises reacting an aldehyde of the general structure II with a ketone of the general structure III, where R1, R2 and R3 are each as defined above, in the liquid phase in a tubular reactor

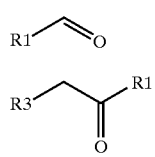

wherein the catalyst is present in the continuous phase and at least one reactant is present in a dispersed phase and the loading factor of the tubular reactor is not less than 0.8.

The aldehydes can contain 1 to 15 carbon atoms, preferably 4 or 5 carbon atoms. The ketones preferably contain 3 to 15 carbon atoms; acetone is used in particular.

R1, R2 and R3 have the same meanings in all the three structural formulae.

The tubular reactor that may be used in the process of the invention can contain packing elements or internal fitments. Packing elements for the purposes of the present invention include for example Raschig rings, saddles, Pall rings, Tellerettes, wire mesh rings, wire mesh fabrics. Examples of internal fitments, internals for short, include filter plates, baffles, column trays, perforated plates or other mixing means. But internals for the purposes of the present invention also include a plurality of narrow parallel tubes forming a multitube reactor. Particular preference is given to structured mixture packings or demister packings.

It is of decisive importance in the process according to the invention to maintain or exceed a minimum cross-sectional throughput loading for the tubular reactor. When the reactor is operated in upflow mode, the flooding point should be exceeded. The reactor is thus operated at above the point at which bubble columns are usually operated. In downflow operation, the cross-sectional throughput loading should be adjusted so that the reactor is completely flooded. Thus, the process is operated at above the point at which it would still be possible to speak of a trickle bed.

To more particularly stipulate the minimum loading to be maintained for the reactor, the loading factor B of the tubular reactor is calculated as a dimensionless pressure drop $$B=PD/PS$$

where PD [Pa/m] is a pressure drop per unit length of the reactor under operating conditions and PS [Pa/m] is a mathematical parameter having the dimensions of a pressure per unit length, defined as the ratio of a mass flow M [kg/s] of all the components in the reactor to the volume flow V [m$^3$/s] of all the components under operating conditions, multiplied by g=9.81 m/s$^2$, i.e., PS=(M/V)*g.

PS may be thought of as the static pressure per meter of a multiphase mixture in an upright tube when all phases flow at the same velocity. PS is a purely mathematical construct which is derived from the streams fed to the reactor and is independent of the flow direction of the reactor, the flow velocity of all phases or flooding condition of the reactor.

The pressure drop PD [Pa/m] is used as a mathematical parameter to stipulate the process conditions and can be calculated by established methods for single-phase or multiphase flows. Appropriate methods of calculating the pressure drop PD in tubes, internal fitments or packed beds etc. may be found for example in the VDI Wärmeatlas, 7th expanded edition, VDI-Verlag GmbH, Düsseldorf 1994, sections La1 to Lgb7, and also in the standard reference Heinz Brauer, Grundlagen der Einphasen-und Mehrphasenströmungen, Verlag Sauerländer, Aarau and Frankfurt/Main, 1971.

The pressure drop PD in the case of a single-phase flow through an empty tube is given by $$PD=Cw*\rho/2*w^2/D$$

where $\rho$ [kg/m$^3$] is the density of the flowing medium under operating conditions, w [m/s] is the flow velocity (volume flow/cross-sectional area), D [m] is the tube diameter and Cw [-] is the resistance coefficient of the tube through which flow occurs.

In the case of a flow through packing, beds or internal fitments, the velocity w must be replaced by the effective velocity (w/$\psi$) and the tube diameter D by the hydraulic channel diameter d$_H$ of the packing or internal fitments, so that:

$$PD=Cw*\rho/2*(w/\psi)^2*1/d_H$$

where d$_H$ [m] is the hydraulic channel diameter, $\psi$ [-] is the empty tube fraction Cw [-] is the resistance coefficient of the packed apparatus through which flow occurs.

The packing-specific data d$_H$ and $\psi$ are frequently part of the supply specifications for packing. The abovementioned VDI Wärmeatlas gives data for a number of packings.

The intertube fraction $\psi$ can also be determined experimentally by, for example, measuring the volume of the reactor before and after filling with the packing. The hydraulic channel diameter can in turn be calculated, if it is not known, from the specific surface area F [m$^2$/m$^3$] of the packings or internals (generally known or experimentally determinable) using the simple relationship dH=4$\psi$/F.

The resistance coefficient of tubes, internals and packings is generally described as a function of the Reynolds number Re, which gives information about the flow state under the chosen conditions. In the case of packings, internals, etc., the following relationship can almost always be employed:

$$Cw=K_1/Re^n+K_2/Re^m$$

where frequently employed values for the indices are n=1, m=0 (method of S. Ergun, Chem. Engng. Progr. 48, (1948), 89) or n=1, m=0.1 (method of Brauer et al.). K$_1$ and K$_2$ are packing-specific constants which are known from supply data or from the literature (examples may be found in the VDI Wärmeatlas and in Brauer et al.). But they can also be determined experimentally by passing a liquid at various velocities through the tubular reactor containing packings and determining Cw as a function of Re from the known data and the measured pressure drop.

The dimensionless Reynolds number Re is finally defined as $$Re=w*(\rho/\eta)*D \text{ for empty tubes or}$$

Re=(w/$\psi$)*($\rho/\eta$)*dH for tubes containing internals or packings. $\eta$[Pa*s] is in each case the viscosity and $\rho$[kg/m$^3$] the density of the flowing medium.

The pressure drop in the case of two phase flows (here liquid-liquid for aldehyde-ketone mixture/catalyst solution) increases disproportionately. Usually, the method of Lockhart-Martinelli (in Brauer et al.) is used to express the pressure drop of the two phase flow P$_{l1l2}$ on the basis of the pressure drop of one of the two phases, for example on the basis of the pressure drop of the pure flowing liquid phase P$_{l1}$, and related to the ratio of the pressure drop of the other phase P$_{l2}$ deemed to be flowing alone.

Pressure drops in two phase flows are frequently calculated using dimensionless pressures $\phi^2$=P$_{l1l2}$/P$_{l1}$ and X$^2$=P$_{l1}$/P$_{l2}$. The further relationship $\phi^2$=function(X$^2$) has been extensively investigated. Examples may be found in the following literature references:

Y. Sato, T. Hirose, F. Takahasi, M. Toda: "Pressure Loss and Liquid Hold Up in Packed Bed Reactor with Cocurrent Gas-Liquid Down Flow"; J. Chem. Chem. Eng. Of Japan, Vol 6 (No. 2), 1973, 147–152;

D. Sweeney: "A Correlation for Pressure Drop in Two-Phase Concurrent Flow in Packed Beds"; AIChE-Journal, Vol. 13, 7/1967, 663–669;

V. W. Weekman, J. E. Myers: "Fluid-Flow Characteristics of Concurrent Gas-Liquid Flow in Packed Beds": AIChE-Journal, Vol 10 (No. 6), 11/1964, 951–957;

R. P. Larkins, R. P. White, D. W. Jeffrey: "Two-Phase Concurrent Flow in Packed Beds"; AIChE-Journal, Vol 7 (No. 2), 6/1961, 231–239 or N. Midoux, M. Favier, J.-C. Charpentier: "Flow Pattern, Pressure Loss and Liquid Holdup Data in Gas-Liquid Down-Flow Packed Beds with Foaming and Nonfoaming Liquids"; J. Chem. Eng. Of Japan, Vol 9 (No. 5), 1976, 350–356.

The calculation is frequently carried out using the Midoux proposal. For example:

$$\phi^2=1+1/X+1.14X^{0.54}$$

This relationship, named for Lockhart-Martinelli, is depicted in graph form in many works; detailed discussions of it may be found in many chemical engineering textbooks and papers, including Brauer et al.

The pressure drop of the two phase flow $P_{l1l2}$ is derived from the pressure drop (experimentally determined or estimated as explained above) of the pure flowing liquid phase $P_{l1}$ using $$P_{l1l2}=\phi^2+P_{l1}$$

Generally, expressed as a function of the reactor length L[m]

$$PD=P_{l1l2}/L.$$

The pressure drop of a multiphase flow can thus be calculated by customary methods of chemical engineering. The same applies to the previously defined dimensionless pressure drop B, i.e., the loading factor of the multiphase reactor.

The magnitude of the dimensionless loading factor B is a necessary condition of the process according to the invention; B should not be less than 0.8, preferably not less than 0.9 or particularly preferably not less than 1. Preferred ranges include 0.8–100, 0.8–20 and 5–16, including all values and sub-ranges therebetween such as 10, 30, 40, 50, 60, 70, 80 and 90.

When B is not less than 0.8, a downwardly operated reactor starts to flood. It is expressly stated that, provided these conditions are observed, the advantages of the process according to the invention are obtained even when the reactor is operated upwardly or in some other direction.

Higher cross-sectional loadings of the reactor (B>>1), identifiable by the increasing pressure difference across the reactor, are possible at any time and even desirable, as long as the increasing space-time yields justify the similarly increasing energy consumption. An upper limit is therefore imposed only by practical considerations such as energy consumption or difficulties with the separation of the phases after the reaction has taken place.

It is thus clear that, as well as the volume flows of the individual phases and the superficial velocities $w=V/(\pi D^2/4)$ derived therefrom, the physical dimensions of the reactor (length L, diameter D) and especially the data for the packings used (hydraulic diameter $D_H$, empty tube fraction $\psi$) play an important part. By correctly choosing these parameters it is easy to optimize the process to a very wide variety of requirements, as long as the stipulation $B\geq 0.8$, preferably $B\geq 0.9$ and particularly preferably $B\geq 1$ is observed.

In the case of a slow reaction, for example, a small hydraulic diameter or a large specific surface area will be chosen for the packings, so that the stipulated conditions for B are even achieved at low flow velocities. This provides adequate residence times across the length of a sensibly dimensioned industrial reactor. In the case of very fast reactions, a converse approach is advisable.

A further criterion governing the practice of the process according to the invention is the ratio of the mass flow of the liquid, catalyst-containing phase $M_1$ to the mass flow of the disperse phase $M_2$. In the present invention, the mass flow of the catalyst phase $M_1$ is substantially greater than the mass flow $M_2$ of the disperse phase. In the process according to the invention, the mass ratio $M_1/M_2$ of the continuous phase ($M_1$) to the disperse phase ($M_2$) can be greater than 2 and is preferably >10. Flow ratios of $M_1/M_2>100$ are entirely possible and frequently even advantageous. Under the condition $M_1/M_2>2$, the catalyst phase is the continuous phase, while the disperse phase is divided into fine droplets.

The size of the fine droplets can be estimated by customary engineering methods. Useful methods include approaches involving dimensionless parameters, for example $$d_s/d_H=k*Re_{l1l2}{}^m*We_{l1l2}{}^n$$

where $d_s$ is the droplet diameter after Sauter (in Brauer et al.)

$d_H$ is the hydraulic diameter of the packing, $Re_{l1l2}$ is the Reynolds number of the multiphase flow= $w_{l1l2}*(\rho/\eta)*(dH/\psi)$, $We_{l1l2}$ is the Weber number of the multiphase flow= $w_{l1l2}{}^2*(\rho/\sigma)*(dH/\psi^2)$, k,m and n are each empirical constants (known or experimentally determined), w is the superficial velocity [m/s]=$V/(\pi D^2/4)$, V is the volume flow under operating conditions [m$^3$/s], $\rho$ is the density under operating conditions [kg/m$^3$], $\eta$ is the viscosity under operating conditions [Pa*s], and $\gamma$ is the interfacial tension under operating conditions [N/m] and the index l1 (denotes the first liquid phase) and the index l2 (denotes the second liquid phase).

In the case of structured packings such as Sulzer-SMV or narrow tubes as internal fitments, it is seemingly plausible that a calculated drop diameter $d_s$ greater than the channel diameter is not sensible. But this does not hold for pervious packings and packing elements such as for example wire mesh rings or wire mesh fabrics (known as demister packings or droplet collectors). The process according to the invention can utilize calculated droplet diameters which are at least equal to or smaller than the hydraulic channel diameter:

$$d_S/d_H \leq 1, \text{ preferably } <0.9.$$

The calculated drop diameter can finally be used to calculate a mass transfer area by $$A_S=6\Phi_{l2}d_s \; [m^2/m^3].$$

For the phase fraction $\Phi_{l2}$ of the disperse phase (the organic phase is dispersed in the case of the aldol condensation), the ratio of the superficial velocities of the phases can be used:

$$\Phi_{l2}=w_{l2}/w_{l1l2}.$$

The residence time $\tau$ of the phases flowing through the reactor is approximately given by $\tau \sim L*\psi/w_{l1l2}$. The residence time $\tau$ in the process according to the invention is generally much less than one hour and can be in the minute range or even lower. Nevertheless, this wholly unusual mode of operation (high catalyst throughput in the reactor, comparatively low fraction of reactant in the reaction mass and hence in turn a very short residence time) provides surprisingly high space-time yields in many multiphase reactions. Alternatively, for the same space-time yields, it is possible to operate at distinctly lower temperatures than is customary, since the increase in the reaction rate, which may entail for example a minimization of secondary reactions and hence improved selectivity, makes this economically feasible.

Advantageously, the reactant or reactants is or are dispersed by the energy introduced into the tubular reactor by the continuous phase.

The process according to the invention can be very flexibly optimized to a very wide variety of requirements.

The following embodiments of the process according to the invention can lend themselves for specific requirements:

For an application requiring a very long mixing zone or a calming zone, for example to take off streams, a cascaded arrangement of tubular reactors containing internals or packings co m mends itself.

A cascaded arrangement of tubular reactors or the alternating arrangement of packed and empty tube sections is advisable when a particularly small pressure drop is desired.

Another possibility is the parallel arrangement of tubular reactors or the use of a multitube reactor, in which case the tubes can assume the function of internal fitments.

The heat removal in the case of strongly exothermic reactions, as in the case of the aldol condensation for example, is similarly uncritical in the process according to the invention. The high throughput of the catalyst circuit acts as a heat transfer medium, so that even in the case of an adiabatic operation of the reactor only small temperature differences arise and a homogeneous temperature distribution without temperature spikes results in the reactor. The heat generated can then be conveniently removed in a conventional heat exchanger disposed in the external catalyst circuit, or be exploited for energy recovery. To improve heat removal, it can sometimes be useful to run the catalyst circuit at a higher circulation rate, i.e., at a higher B value, than is necessary according to the experimental results, since the catalyst circuit enables a smaller temperature gradient to be set across the reactor.

Compared with the prior art, the process according to the invention offers appreciable advantages, for example:

High space-time yields can be achieved at comparatively low temperatures.

By-product formation is extremely low.

The catalyst lasts longer, deactivation is minimal, continuous loss from the system is minimized.

When the process according to the invention is used for preparing α,β-unsaturated ketones by aldol condensation of an aldehyde with a ketone, there is a further advantage in that, owing to the high reaction rates, even aldehydes having a very low solubility in the catalyst phase can be economically converted into the corresponding aldol condensation products.

Useful solvents for preparing the catalyst solution or phase include all solvents which meet the following conditions:

The solvent is sparingly soluble in the product phase.

The product is only sparingly soluble in the catalyst phase, which consists of catalyst and solvent.

The solvent possesses sufficient solvent power for the catalyst used.

A preferred solvent for the catalyst is water or a homogeneous mixture of water and an organic solvent. The catalyst phase can also contain more than one solvent, for example water and diethylene glycol.

Optionally, the catalyst phase can contain phase transfer, surface-active or amphiphilic reagents or surfactants.

Useful catalysts include water-soluble basic compounds, for example hydroxides, bicarbonates, carbonates or carboxylates in the form of their alkali or alkaline earth metal compounds. Preference is given to using aqueous alkali metal hydroxide solutions.

The concentration of the catalyst in the catalyst solution is preferablyt between 0.1 and 15 mass %, especially between 0.1 and 5 mass %.

The process according to the invention is useful for reacting an aldehyde (structure II) with a ketone (structure III) capable of undergoing an aldol condensation reaction. Since the aldehyde used in this reaction constitutes the reactive carbonyl unit, there are no restrictions with regard to the structure of the aldehyde. Ketones constitute the methylene component in this reaction. Useful ketones must accordingly have two α-hydrogen atoms on the same carbon atom.

Useful aldehydes for the reaction according to the invention include for example the following:

formaldehyde, acetaldehyde, propanal, n-butyraldehyde, isobutyraldehyde, crotonaldehyde, valeraldehyde, 2-methylbutanal, 3-methylbutanal, dimethylolpropanal, tiglic aldehyde, 3,3-dimethylacrolein, n-hexanal, isohexanal, n-heptanal, citral, α- and β-cyclocitral, benzaldehyde, cinnamaldehyde, phenylacetaldehyde, hydrocinnamaldehyde, 2-phenylpropionaldehyde, cyclohexylcarbaldehyde, anisaldehyde, farnesal, phytal, vitamin A aldehyde.

It is further possible to use aldehydes or aldehyde mixtures obtained by hydroformylation of olefins or olefin mixtures. Useful examples are the $C_5$ aldehyde mixtures which are obtained in the hydroformylation of $C_4$ olefin mixtures, or the isomeric isononanals, which are formed in the hydroformylation of technical grade dibutene mixtures.

Useful aldehydes further include unsaturated aldehydes formed by self-condensation of an aldehyde, such as 2-ethylhex-2-enal from n-butyralaldehyde.

Useful ketones of the formula III include for example:

acetone, methyl ethyl ketone, methyl n-propyl ketone, methyl isopropyl ketone, methyl n-butyl ketone, methyl isobutyl ketone, methyl tert-butyl ketone, diethyl ketone, diacetyl, 6-methyl-5-hepten-2-one, 6-methyl-3-hepten-2-one, acetophenone, cyclohexanone, cyclohexyl ethyl ketone, benzyl methyl ketone, methyl propenyl ketone, ethyl propenyl ketone, mesityl oxide, propyl propenyl ketone, isobutylidene acetone, 6-methyl-3,5-heptadien-2-one, β-ionone, farnesyl acetate, geranyl acetate, cyclooctanone, isophorone, 3,3,5-trimethylhexanone, cyclodecanone.

Both the aldehyde and the ketone used can be solid or liquid under reaction conditions. (Formaldehyde is used as a solution, preferably in water.) When the mixture of reactants is solid or a solid reactant is fed on its own into the reactor, a solvent has to be used. Useful solvents include liquids which are inert under reaction conditions and which are substantially insoluble in the catalyst solution. It is similarly necessary to use a solvent when the product formed is solid.

In addition, the use of an organic solvent which is only sparingly soluble in the catalyst phase can have further advantages. This solvent can additionally be readily soluble in the product phase. For example, the addition of a solvent can raise the selectivity for the formation of the target product. Moreover, the use of a solvent can make it easier to control the reaction and work up the reaction mixture, as will be described hereinbelow. The converse is also conceivable, namely the use of a solvent which is readily soluble in the catalyst phase but not readily soluble in the product phase.

Useful solvents include for example ethers or hydrocarbons. A preferred solvent is cyclohexane.

The two reactants can be fed separately or as a mixture into the reactor.

The molar ratio between aldehyde and ketone is preferably in the range from 2/1 to 1/10, more preferably in the range from 1/1 to 1/3.

The specific residence time and the loading factor must be chosen in accordance with the particular process of the invention, and is within the skill of the ordinary artisan in view of this disclosure. One or more tubular reactors having internal fitments can be used for this purpose in accordance with the preceding description.

The reaction according to the invention can be carried out in a temperature range from 30° C. to 200° C., preferably in the range from 60° C. to 150° C.; the overall pressure is preferably between 0.1 bar and 25 bar.

The phases can flow through the reaction tube in cocurrent in the downward or upward direction. For safety reasons, preference is given to feeding the phases in from the top.

The heat of reaction can be removed via various heat exchangers. The heat exchangers do not have to be in the vicinity of the reaction space, but can also be anywhere outside the reactor. The individual heat flows are dependent on the specific heat of reaction and also on the temperatures desired in the reactor and in the workup means.

The removed heat of reaction is thus very simple to utilize, for example in the process itself, for heating a distillation apparatus or for generating steam.

The liquid mixture leaving the reactor is mechanically separated in a liquid-liquid separation vessel into catalyst phase and product phase. This can be accomplished in settling vessels of various designs or in centrifuges. Settling vessels are preferable for cost reasons.

The residence times in the separation apparatus are not critical per se, but they are advantageously kept short. This has the following advantages: the separation apparatus is small and its capital cost correspondingly low. When residence times are short, virtually no side reactions occur in the separation vessel. For the separation of the phases to occur quickly, the density difference between the two phases has to be sufficiently large and their viscosities have to be low. All three parameters are a function of the temperature and can easily be determined by preliminary experiments, within the skill of the ordinary artisan.

In addition, the density and viscosity of the catalyst solution can be varied by the choice of solvent and catalyst concentration. A further possibility is to alter the density and viscosity of the product phase by addition of a solvent. Phase separation can be effected over a wide temperature range. The separation temperature can be higher than the temperature of the reactor effluent at the reactor outlet. For energy reasons, however, it is disadvantageous to employ a higher temperature than the liquid temperature at the reactor outlet. The lowest possible temperature must be the pour point of one of the two liquid phases. With an eye on short separation times, however, excessively low temperatures are preferably not used, as mentioned above.

The water of reaction formed has to be removed from the reaction system. When the amount of water removed with the organic product phase is larger than the amount formed in the course of the reaction, the difference has to be continually replenished. It is simpler to conduct the reaction in such a way that the amount of water removed with the organic product phase is exactly equal to the amount formed in the course of the reaction. The solubility of the water in the product phase and the associated amount of water therein can be adjusted by addition of a solvent, so that the use of a solvent can be advantageous.

When, in contrast, the catalyst solution is diluted by the water of reaction, a portion of the water has to be removed therefrom. This can be accomplished by distilling water out of the catalyst solution. Optionally, the reaction mixture can be flashed prior to phase separation to concentrate the catalyst solution.

Water can be removed from the removed organic product phase by distillation. This is particularly simple when water can form a minimum heteroazeotrope with a component of the product phase present in sufficient quantity. This case can be achieved, regardless of the reaction partners, by addition of an appropriate solvent, for example cyclohexane, to form a minimum heteroazeotrope with water.

The product stream is separated according to known processes, for example by distillation, into product, reactant, by-product and, where appropriate, solvent. The removed reactants and any solvent are recycled into the process. It is similarly advantageous to recycle a portion of the by-products, namely the addition products, to increase the selectivity of the reaction.

The removed catalyst solution is recycled into the reactor, where appropriate after removal from the system of a small portion and appropriate replenishment with fresh catalyst solution.

The $\alpha,\beta$-unsaturated ketones produced in the process according to the invention can be hydrogenated to the corresponding saturated ketones.

The compounds prepared according to the process of the invention are useful intermediates for preparing, e.g., scents, solvents, dyes, plastics and pharmaceuticals. For instance 6-methylhept-3-en-2-one is an important intermediate for the synthesis of vitamin E. Some of these materials are themselves used as a scent. Furthermore, the unsaturated ketones can be hydrogenated to the saturated alcohols, which can be used to prepare esters or olefins for example.

The examples hereinbelow describe the invention without restricting its scope, which is defined in the claims.

The first table accompanying the examples describes first the catalyst composition in mass percent, then the amount of reactant and its composition in mass percent derived from analysis by gas chromatography.

The lower part of each second table lists the product composition, likewise in mass percent derived from analysis by gas chromatography.

The upper part of the second table reports the space-time yield (STY), the conversion (C) of the aldehydes, the selectivity (S) to the desired aldol condensation products and the loading factor (B) (except for example 1). With regard to the catalyst composition described, it is to be noted that initial values are concerned in the examples. The fraction of NaOH was slightly diluted by the water of reaction from the aldol condensation. In addition, the parallel Cannizzaro reaction causes the alkaline catalyst to become neutralized. But both the effects are so slight in the period under review that this is immaterial to the description of the experiments and the experimental results.

EXAMPLE 1 (COMPARATIVE)

This example describes a process for the aldol condensation of acetone (Ac) and 3-methylbutanal (3-MBA) to 6-methyl-3-hepten-2-one (6-MH). This comparative example employs the traditional stirred tank technology. The formation of the by-products 4-methyl-3-penten-2-one (4-MP), 3-methyl-2-isopropyl-2-butenal (3-MiPB), 5-methyl-2-isopropyl-2-hexenal (5-MiPH), 4-hydroxy-6-methylheptan-2-one (6-HMH) and the other high boilers (HS) are reported in % by weight in the table hereinbelow.

The stirred tank reactor was initially charged with 1,000 g of catalyst. The reactant mixture was added. The reaction was carried out at 80° C. under the autogenous pressure of the reaction participants.

| | |
|---|---|
| Catalyst [g] | 1000 |
| c NaOH [wt %] | 7 |
| Water [wt %] | 89 |
| Acetone [wt %] | 4 |
| Reactant [1/h] | 424 |
| Ac [wt %] | 28.6 |
| 3-MBA [wt %] | 38.2 |
| CH [wt %] | 33.2 |

The following result was obtained:

| | |
|---|---|
| STY [t/m³/h] | 1.4 |
| C | 0.75 |
| S | 0.67 |
| Ac | 23.61 |
| 3-MBA | 10.10 |
| 6-MH | 44.37 |
| 4-MP | 0.16 |
| 3-MiPB | 0.27 |
| 5-MiPH | 0.72 |
| 6-HMH | 17.38 |
| HS | 3.39 |

Re examples 2 and 3

The aldolization was carried out in an experimental apparatus which is diagramed in FIG. 1. A pump 1 recirculates the continuous catalyst phase 2. The catalyst is admixed with the aldehyde or aldehyde mixture through line 3 or with various aldehydes separately through lines 3 and 4. The hereinbelow recited examples 2 and 3 were each carried out by adding the reactants exclusively via line 3. The multiphase mixture 5 in examples 3 to 14 is pumped through the tubular reactor 6, which is 3 m in length and 17.3 mm in diameter and equipped with static mixing elements 2 mm in hydraulic diameter. The resulting mixture 7, consisting of the reaction product, unconverted reactant and the catalyst, can be freed of volatile constituents in the gas separator 8 by removal into line 9. This line was closed for the hereinbelow recited examples other than 2.

The liquid stream 10 downstream of the devolatilizing stage 8 is passed into a phase separation vessel 11. Here the aqueous catalyst phase 2 is separated off and returned into the circuit. The organic phase, which passes over a weir and contains the reaction product, is removed from line 12.

The heat of reaction can be removed via heat exchangers 13, 14 and 15 which are situated outside the reactor.

EXAMPLE 2

This example describes the process according to the invention for the aldol condensation of acetone (Ac) and 3-methylbutanal (3-MBA) to 6-methyl-3-hepten-2-one (6-MH). The formation of the by-products 4-methyl-3-penten-2-one (4-MP), 3-methyl-2-isopropyl-2-butenal (3-MiPB), 5-methyl-2-isopropyl-2-hexenal (5-MiPH), 4-hydroxy-6-methylheptan-2-one (6-HMH) and the other high boilers (HS) are reported in % by weight in the table hereinbelow.

The reactor was operated with a catalyst space velocity of 400 kg/h at 80° C. under the autogenous pressure of the reaction participants.

| | |
|---|---|
| Catalyst [kg] | 4.5 |
| c NaOH [%] | 6.7 |
| Water [%] | 89.2 |
| Acetone | 4.1 |
| Reactant [1/h] | 5.24 |
| Ac [wt %] | 42.36 |
| 3-MBA [wt %] | 33.34 |
| CH [wt %] | 24.30 |

The following result was obtained:

| | |
|---|---|
| STY [t/m³/h] | 3.2 |
| C | 0.86 |
| S | 0.95 |
| B | 15.34 |
| Ac | 33.27 |
| 3-MBA | 5.26 |
| 6-MH | 58.37 |
| 4-MP | 0.66 |
| 3-MiPB | 0.42 |
| 5-MiPH | 0.3 |
| 6-HMH | 0.5 |
| HS | 1.2 |

It is clear that the process according to the invention provides distinctly higher selectivities coupled with higher space-time yields.

EXAMPLE 3

This example describes the process according to the invention for the aldol condensation of acetone (Ac) and pentanal (PAL) to 3-octen-2-one (3-ON). The formation of the by-products 4-methyl-3-penten-2-one (4-MP), 4-hydroxy-4-methyl-3-pentan-2-one (4-HMP), 4-hydroxy-3-octen-2-one (4-HON), 2-propyl-2-heptenal (2-PHL) and also the other high boilers (HS) are reported in weight % in the table hereinbelow.

The reactor was operated with a catalyst space velocity of 400 kg/h at 80° C. under the autogenous pressure of the reaction participants.

| | |
|---|---|
| Catalyst [g] | 4981 |
| c NaOH [%] | 4.0 |
| Water [%] | 91.8 |
| Acetone | 4.2 |
| Reactant [1/h] | 4.28 |
| Ac [wt %] | 48.04 |
| 3-MBA [wt %] | 51.96 |

The following result was obtained:

| | |
|---|---|
| STY [t/m³/h] | 2.1 |
| C | 0.95 |
| S | 64.00 |
| B | 14.72 |
| Ac | 22.52 |
| PAL | 3.04 |
| 4-MP | 0.35 |
| 4-HMP | 0.23 |
| 3-ON | 47.46 |

| | |
|---|---|
| 4-HON | 8.03 |
| 2-PHL | 9.49 |
| HS | 8.88 |

All patents and other publications mentioned herein are incorporated herein by reference, as is German patent application 10106186.2 filed Feb. 10, 2001.

What is claimed is:

1. A process for preparing an α,β-unsaturated ketone of the formula I

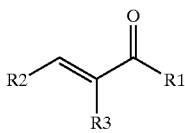

where R1 and R2 each independently represent a branched or unbranched, saturated or unsaturated aliphatic or cycloaliphatic-aliphatic hydrocarbon radical of 1 to 20, carbon atoms or a saturated or unsaturated cycloaliphatic hydrocarbon radical of 5 to 12 carbon atoms which may contain alkyl groups as substituents, or an endoalkylene group or an araliphatic hydrocarbon radical of 7 to 15 carbon atoms, or an aromatic hydrocarbon radical, R3 represents hydrogen or an aliphatic hydrocarbon radical of 1 to 10 carbon atoms, wherein R1 and R3 may combine with the two adjacent carbon atoms to form members of a common alicyclic ring and wherein in R1, R2 and R3 one or more methylene groups which are not α-disposed relative to a carbonyl group may be substituted by an oxygen or sulfur atom, which process comprises reacting an aldehyde of the formula II with a ketone of the formula III, where R1, R2 and R3 are each as defined above, in the liquid phase in a tubular reactor

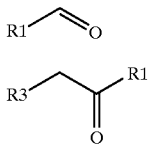

wherein the catalyst is present in the continuous phase and at least one reactant is present in a dispersed phase and a loading factor B of the tubular reactor is not less than 0.8.

2. A process as claimed in claim 1, wherein formula II is an aldehyde of 1 to 15 carbon atoms are used.

3. A process as claimed in claim 1, wherein formula II is an aldehyde of 4 or 5 carbon atoms.

4. A process as claimed in claim 1, wherein formula III is a ketone of 3 to 15 carbon atoms.

5. A process as claimed in claim 4, wherein the formula III ketone is acetone.

6. A process as claimed in claim 5, wherein the catalyst is a water-soluble basic compound.

7. A process as claimed in claim 6, wherein the catalyst is selected from the group consisting of hydroxides, bicarbonates, carbonates, carboxylates and their mixtures, all in the form of their alkali or alkaline earth metal compounds.

8. A process as claimed in claim 7, wherein the catalyst is present in the continuous phase in a concentration of 0.1 to 15 mass %.

9. A process as claimed in claim 1, wherein the continuous phase is water or a homogeneous mixture of water and an organic solvent.

10. A process as claimed in claim 9, wherein water is the continuous phase.

11. A process as claimed in claim 9, wherein a mixture of water and ethylene glycol is the continuous phase.

12. A process as claimed in claim 1, wherein the loading factor B is not less than 0.9.

13. A process as claimed in claim 1, wherein the loading factor B is not less than 1.0.

14. A process as claimed in claim 1, wherein the mass ratio of continuous phase to dispersed phase is greater than 2.

15. A process as claimed in claim 1, wherein the aldehyde and ketone are dispersed by energy introduced into the tubular reactor by the continuous phase.

16. A process as claimed in claim 1, wherein the aldehyde and the ketone are present in a molar ratio in the range from 2/1 to 1/10.

17. A process as claimed in claim 1, wherein the continuous phase comprises solvent that is readily soluble in a product phase and sparingly soluble in a catalyst phase.

18. A process as claimed in claim 1, wherein the continuous phase solvent is readily soluble in a catalyst phase and sparingly soluble in a product phase.

19. A process as claimed in claim 18, wherein the solvent forms a minimum heteroazeotrope with water.

20. A process as claimed in claim 18, wherein the solvent is cyclohexane.

21. A process as claimed in claim 1, wherein the α,β-unsaturated ketone produced are hydrogenated to form a corresponding saturated ketone.

22. A process as claimed in claim 1, wherein the α,β-unsaturated ketone produced is hydrogenated to form a corresponding saturated alcohol.

23. A process ad claimed in claim 6, whereint the catalyst is an aqueous alkali metal hydroxide solution.

24. A process as claimed in claim 7, wherein the catalyst is present in the continuous phase in a concentration of 0.1 to 5 mass %.

25. A process as claimed in claim 1, wherein the aldehyde and the ketone are present in a molar ratio in the range from 1/1 to 1/13.

* * * * *